United States Patent [19]

Loeffler

[11] 4,114,811
[45] Sep. 19, 1978

[54] SPRAY DISPENSER WITH EASILY ACTUABLE MOUTHPIECE

[75] Inventor: Herbert H. Loeffler, Arlington, Mass.

[73] Assignee: Ciba-Geigy Corporation, Ardsley, N.Y.

[21] Appl. No.: 786,945

[22] Filed: Apr. 12, 1977

[51] Int. Cl.$^2$ ............... A61M 15/00; B05B 1/28
[52] U.S. Cl. ............... 239/288.5; 128/173 R; 128/208; 222/182; 239/499; 239/507; 239/516
[58] Field of Search ............... 239/288–288.5, 239/499, 504, 505–508, 516–519, 521, 523; 128/173 R, 203, 208; 222/182, 402.13, 402.14

[56] References Cited

U.S. PATENT DOCUMENTS

| | | | |
|---|---|---|---|
| 3,012,555 | 12/1961 | Meshberg | 128/208 X |
| 3,107,670 | 10/1963 | Silson et al. | 128/173 R |
| 3,191,867 | 6/1965 | Helms | 239/288.5 |
| 3,209,751 | 10/1965 | Wakeman | 128/173 R |
| 3,506,004 | 4/1970 | Mann et al. | 128/173 R X |
| 3,622,053 | 11/1971 | Ryden | 128/173 R X |
| 3,739,950 | 6/1973 | Gorman | 128/173 R X |

*Primary Examiner*—John J. Love
*Assistant Examiner*—Andres Kashnikow

[57] ABSTRACT

A spray dispenser for dispensing a spray of a liquid material has a cylindrical container with a nozzle adjacent one end thereof directed generally at a right angle to the longitudinal axis of the container. A mouthpiece of resilient material is pivotally mounted on the one end of the container so that in the storage position it has the axis aligned with the longitudinal axis of the container and it is easily pivoted to the dispensing position at right angles to the axis of the container and around the nozzle by simple pressure on the non-dispensing end thereof and is easily pivoted back to the storage position by pressure on the dispensing end.

3 Claims, 9 Drawing Figures ary4,114,811

SPRAY DISPENSER WITH EASILY ACTUABLE MOUTHPIECE

This invention relates to a spray dispenser for dispensing medication, and more particularly to such a dispenser which has a snap-down mouthpiece thereon.

BACKGROUND OF THE INVENTION AND PRIOR ART

In recent years, medications have increasingly been packaged in aerosol form for dispensing as inhalents. They have been particularly effective in dispensing inhalents in a finely divided spray which is inhaled directly and drawn into the lungs for direct action on the lung tissues. Many medications requiring prompt administration at the onset of a condition, such as asthma, can best be administered in this fashion, because the medication acts directly on the affected tissues. Further, many medications which are required to be fast acting can best be administered in this fashion because the rate of absorption from the lungs is much faster than when the drug is administered orally, and in many instances is as rapid as when the drug is injected.

The medications are usually packaged in containers with a valve and nozzle arrangement through which the spray of medication is dispensed by pressing on a valve actuator on the top or bottom of the container to open the valve, and pressure within the container, either by virtue of a propellant within the container or by air pressure developed by the actuation of the valve actuator, causes dispensing of the material in a finely divided spray.

In order to direct the medication into the oral cavity for inhalation, a funnel-like mouthpiece of some type is required. This must be positioned over the nozzle through which the medication is dispensed from the dispenser, and to project outwardly from the container. Because the containers must be able to be held either upright or upside down, depending upon their design, to operate properly, the dispensing nozzle is usually directed at right angles to the longitudinal axis of the container. The dispensers and the mouthpieces are generally made of plastic. A protective cover is usually required to keep the inside of the mouthpiece and the nozzle clean.

A disadvantage common to all of the currently available dispensers is that the patient must normally remove the protective cover from the mouthpiece, then remove the mouthpiece from a position in which it covers the top of the container, and replace it on the container in the operative position. Dispensers have been developed which have mouthpieces pivoted to the container, but these are all rather cumbersome, and usually require several manipulative actions to bring the mouthpiece from the storage position in which the axis of the mouthpiece is aligned with the axis of the container, to the dispensing position in which the axis of the mouthpiece is substantially perpendicular to the axis of the container. In the case of a patient undergoing an asthmatic attack, or an attack of angina, or a patient who is acutely ill or may have tremors, this action may be a difficult procedure to carry out.

It would be a distinct advance in the art to have a container construction incorporating a mouthpiece in which the mouthpiece could be quickly and easily snapped from the conventional storage position where it protects the nozzle and its interior, into the dispensing position, and when the use of the dispenser is ended, can be just as easily and quickly snapped back into the storage position. It would be a further advantage if this could be accomplished without the necessity of removing a part from the dispenser.

OBJECTS AND BRIEF DESCRIPTION OF THE INVENTION

It is the object of the present invention to provide a dispenser for dispensing a spray of medication from a container and which has a mouthpiece incorporated therewith, which, in the storage position, has the longitudinal axis thereof aligned with the longitudinal axis of the container for the medication, and which in the dispensing condition has the axis thereof perpendicular to the axis of the container, and which mouthpiece can be simply and easily snapped from the storage position to the dispensing position, and can just as easily be snapped from the dispensing position back to the storage position, and which mouthpiece is not removed from the dispenser during movement from the storage to the dispensing position and back.

This object is achieved according to the present invention by the combination of a dispenser for dispensing a spray of a liquid material and having a cylindrical container with a nozzle adjacent one end thereof directed generally at a right angle to the longitudinal axis of the container, and an actuator on the container for actuating the dispenser for dispensing the spray through the nozzle, and a mouthpiece of a resilient material and having a cylindrical portion having an inner cross-sectional shape the same as the external cross-sectional shape of the container and having a slit therein parallel to the longitudinal axis thereof and a loop across one end thereof extending transversely to a diametral line from the slit to the other side of said cylindrical portion, pivot means connected between the point on said cylindrical portion of said mouthpiece at the opposite end of said diametral line and the end structure of the container at the end adjacent which said nozzle is located and on a line parallel to the longitudinal axis of the container through said nozzle, the nozzle being located inwardly along the container from the position of said pivot means a distance substantially half the diameter of the cylindrical portion.

BRIEF DESCRIPTION OF THE DRAWINGS

This object and other objects of the present invention will become apparent from the following description of a preferred embodiment of the invention, taken together with the accompanying drawings, in which.

DETAILED DESCRIPTION OF THE INVENTION

The dispenser according to the present invention comprises a conventional medication holding container 10, either of the aerosol type or of the type which can be pressurized with air by the pressing down of a valve actuator 11. The details of the interior of the container are not shown, since they are conventional and can be found in the aerosol dispenser art. It is sufficient for an understanding of the present invention to point out that the medication is dispensed in a spray from a nozzle 17 directed laterally of the container 10 at a right angle to the longitudinal axis X—X thereof. The exterior shape of container 10 is here shown as that of a right circular cylinder, but for purposes of this invention the term "cylindrical" when used to describe the shape of the container is intended to include other cylindrical shapes, such as those with an oval, cross-section and the like.

Figure 1:
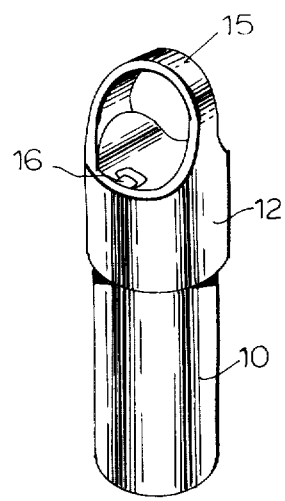
FIG. 1 is a front perspective view of the dispenser according to the present invention with the mouthpiece in the storage position.
Figure 2:
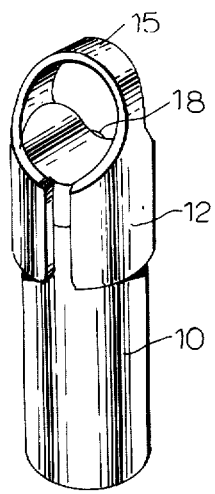
FIG. 2 is a rear perspective view of the dispenser of FIG. 1.

The mouthpiece 12 according to the present invention has a cylindrical portion 13 which has an inner cross-sectional shape substantially the same as the external cross-sectional shape of the container 10, and which in the storage position of the mouthpiece is tightly positioned around the upper end of the storage container 10 with the longitudinal axis thereof aligned with the axis of the container. In the rear of the cylindrical portion 13 of the mouthpiece with respect to the position of the nozzle 17, and as seen in FIGS. 1 and 2, is a slit 14. The non-dispensing end of the cylindrical portion 13 of the mouthpiece has a loop 15 extending thereacross, which, when the mouthpiece is in the storage position, as shown in FIGS. 1-5 and 7, projects upwardly above the pushbutton actuator 11.

The mouthpiece 12 is made of a resilient plastic material, such as polyethylene or polypropylene.

On the container 10 at the rear of the cylindrical portion 13 is a projection 18, the purpose of which is described hereinafter.

At the front of the cylindrical portion 13, diametrally opposite the slit 14 when it is in the storage position, as seen in FIGS. 1-5 and 7, is a hinge member 16 which hinges the periphery of the cylindrical portion of the mouthpiece 12 to the surface of the pushbutton actuator 11. This hinge is attached to the pushbutton actuator 11 at a position directly above the dispensing nozzle 17 along a line parallel to the longitudinal axis of the container 10 and passing through the nozzle 17. The nozzle 17 is positioned below the hinge 16 a distance about half the diameter of the cylindrical portion of the mouthpiece. The loop 15 extends transversely to the diametral line between the hinge 16 and the slit 14.

With the mouthpiece 12 in the storage position as shown in FIGS. 1-5 and 7, because the cylindrical portion 13 fits tightly around the upper part of the dispensing container 10, it protects the nozzle and the inside of the mouthpiece and it does not make the container appreciably larger than the container would be if no mouthpiece were mounted thereon. The loop 15 projects only a short distance above the top of the pushbutton actuator 11, and since, in the embodiment shown, it is narrower than the diameter of the mouthpiece 12, it does not unduly increase the length or bulk of the overall dispenser. The projection 18 is accommodated in the slit 14.

Figure 7:
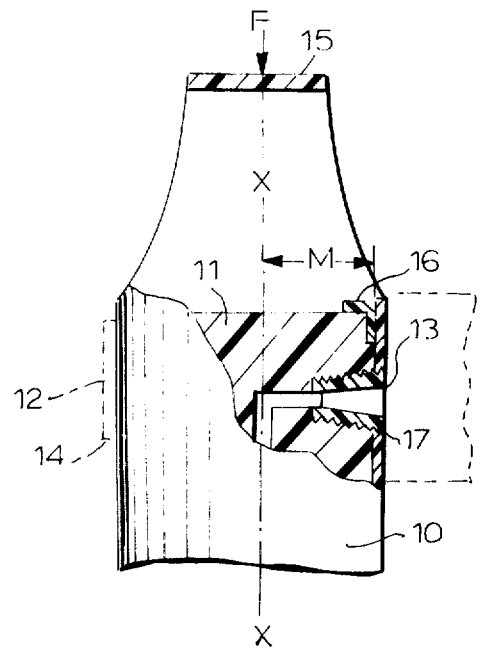
FIG. 7 is a partial sectional view, on an enlarged scale, showing the upper portion of the dispenser with the mouthpiece in the storage position.
Figure 3:
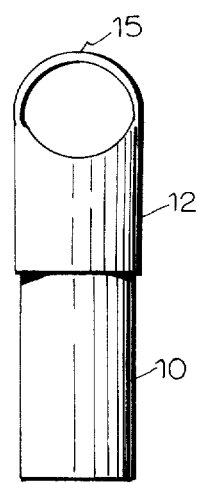
FIG. 3 is a front elevation view of the dispenser of FIG. 1.
Figure 4:
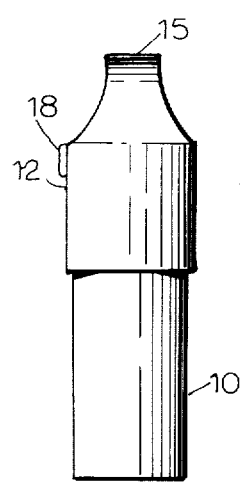
FIG. 4 is a side elevation view of the dispenser of FIG. 1.
Figure 5:
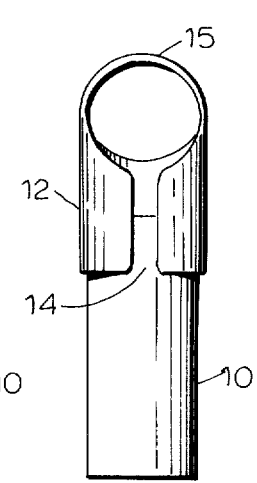
FIG. 5 is a rear elevation view of the dispenser of FIG. 1.
Figure 6:
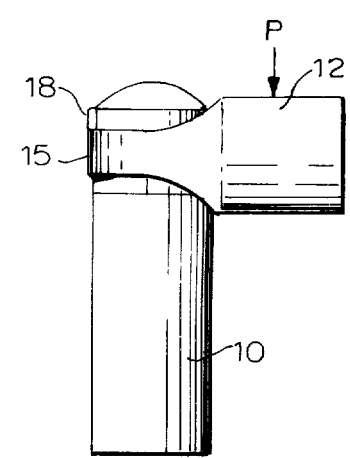
FIG. 6 is a side elevation view similar to FIG. 4 showing the mouthpiece in the dispensing position.
Figure 8:
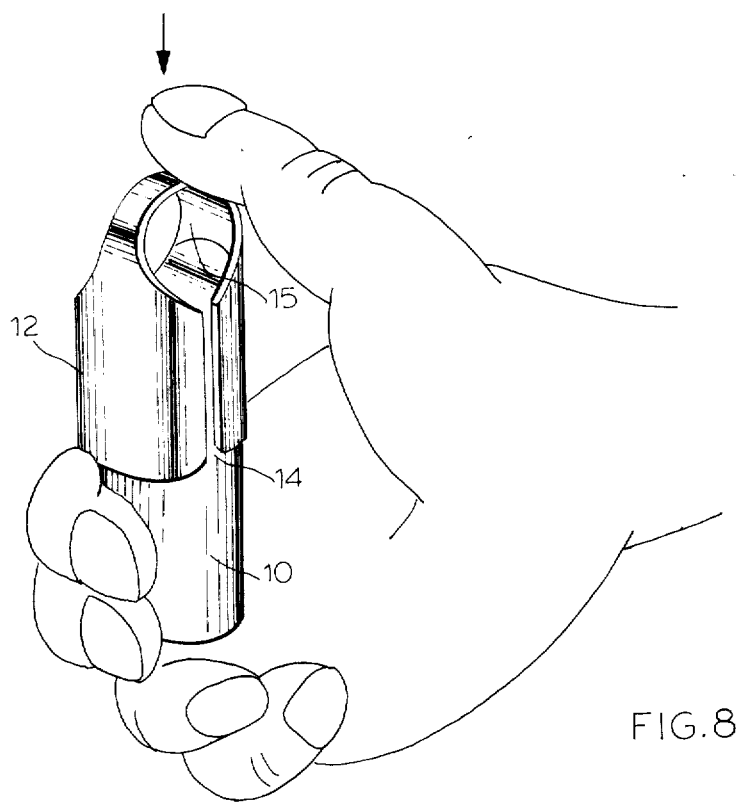
FIG. 8 is a perspective view of the dispenser with the mouthpiece in the storage position and having the force F exerted thereon by a thumb of a hand of a user.

In order to swing the mouthpiece 12 from the storage position shown in FIGS. 7 and 8 to the dispensing position as shown in FIG. 6 and in which the longitudinal axis thereof is at a right angle to the longitudinal axis of the container 10, a force F is exerted on the top of the loop 15, for example by the thumb or the forefinger of the user. It will be seen that this force exerts a moment at the end of a moment arm M extending between the position of the hinge 16 and the longitudinal axis of the container 10 which tends to swing the mouthpiece 12 about the hinge 16 as a pivot. Since the mouthpiece is made of a resilient plastic material, the parts of the mouthpiece on the opposite sides of the slit 14 will be forced away from each other and the edges of the mouthpiece on the opposite sides of the slit 14 will move along the wall of the container 10 until the edges have passed the largest diameter portion of the container 10 in the direction of movement of the slit 14. Thereafter, the resilient force tending to return the thus distorted mouthpiece to its normal shape will force the edges of the slit against the wall of the container and further swing the mouthpiece around the hinge 16 until the loop 15 snaps over projection 18 and lies against the side of the container 10 diametrally opposite the position of the nozzle 17, at which time the mouthpiece will be in the position shown in FIG. 6. At this point, the axis of the mouthpiece is substantially aligned with the nozzle 15, and is transverse to the longitudinal axis of the container 10. The mouthpiece is now ready for dispensing of the spray of medication therethrough by pressure exerted on the actuator 11, which is now exposed at the top of the container 10. Projection 18 bearing against loop 15 holds the mouthpiece firmly in this position.

In order to draw the medication deeply into the lungs, the user inhales while operating the dispenser. The slit 14 provides an opening to allow this air to enter the mouthpiece.

Figure 9:
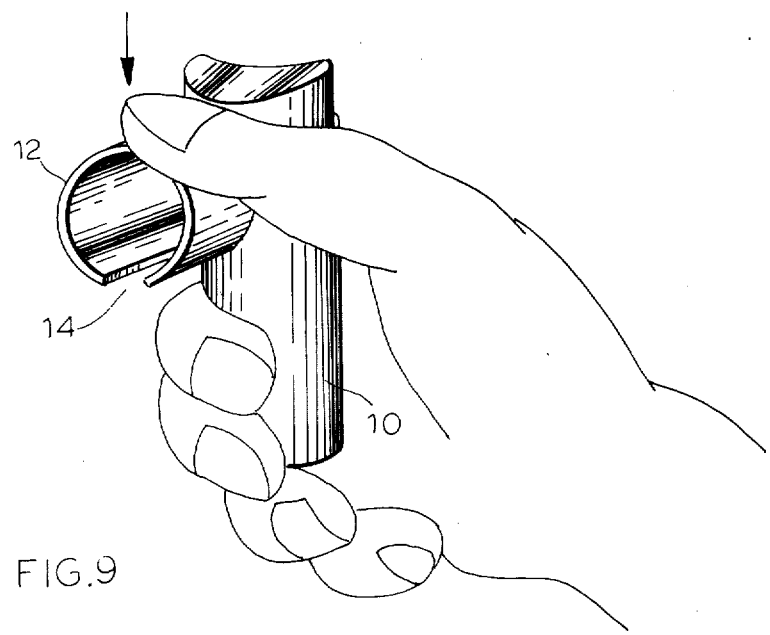
FIG. 9 is a perspective view of the dispenser with the mouthpiece in the position of FIG. 6 showing pressure being exerted thereon by the thumb of the hand of the user.

When dispensing of the medication has ended, simple finger pressure P on the dispensing end of the mouthpiece, as shown in FIGS. 6 and 9 will again pivot the mouthpiece, this time in the opposite direction from the above-described pivoting movement, around the hinge 16, again spreading the portions of the mouthpiece on opposite sides of the slit 14 until the largest diameter portion of the container is reached, after which the resiliency of the mouthpiece will again tend to swing the mouthpiece further toward the storage position, until the mouthpiece finally snaps tightly around the container 10, having returned to the position shown in FIGS. 1-5 and 7.

It will thus be seen that by a simple structure of plastic material, the various parts of which are easily molded and attached to a conventional dispenser, a dispenser with an easily positionable mouthpiece has been provided, which dispenser, when the mouthpiece is in the storage position, is as substantially compact as when it has no mouthpiece thereon, and yet which can be actuated to move the mouthpiece to the dispensing position by simple finger pressure on the loop on the non-dispensing end of the mouthpiece. Further, this invention has provided such a mouthpiece which is also easily returned to the storage position by simple pressure on the dispensing end of the mouthpiece.

While the mouthpiece has been shown as being hinged to the valve actuator 11, it will be appreciated that this is because the nozzle 17 is adjacent the same end of the container 10 at which the actuator is located. If the nozzle is at the other end, the mouthpiece can be hinged directly to the container.

What is claimed is:

1. In combination, a dispenser for dispensing a spray of a liquid material and having a cylindrical container with a nozzle adjacent one end thereof directed generally at a right angle to the longitudinal axis of the container, and an actuator on the container for actuating the dispenser for dispensing the spray through the nozzle, and a mouthpiece of a resilient material and having a cylindrical portion having an inner cross-sectional shape the same as the external cross-sectional shape of the container and having a slit therein parallel to the longitudinal axis thereof and a loop across one end thereof extending transversely to a diametral line from the slit to the other side of said cylindrical portion, pivot means connected between the point on said cylindrical portion of said mouthpiece at the opposite end of said diametral line and the end structure of the container at the end adjacent which said nozzle is located and on a line parallel to the longitudinal axis of the container through said nozzle, the nozzle being located inwardly along the container from the position of said pivot means a distance substantially half the diameter of the cylindrical portion.

2. The combination as claimed in claim 1 in which said pivot means is a hinge connected between said mouthpiece and said container structure.

3. The combination as claimed in claim 1 in which said container has a projection thereon diametrically opposite the nozzle and adjacent the end of the container on which the mouthpiece is mounted and over which the loop snaps when the mouthpiece is pivoted to the position perpendicular to the container.

* * * * *